United States Patent [19]

Chih Wu

[11] 3,936,360

[45] Feb. 3, 1976

[54] PROCESS FOR DISTILLATION AND RECOVERY OF OLEFINIC NITRILES

[75] Inventor: Hsin Chih Wu, Parma, Ohio

[73] Assignee: The Standard Oil Company, Cleveland, Ohio

[22] Filed: Feb. 9, 1973

[21] Appl. No.: 330,980

Related U.S. Application Data

[63] Continuation-in-part of Ser. No. 132,008, April 7, 1971, abandoned.

[52] U.S. Cl. ............... 203/75; 203/42; 203/DIG. 3; 260/465.9; 203/38; 203/34
[51] Int. Cl.² ...................... B01D 3/00; B01D 3/10
[58] Field of Search ............ 203/42, 34, 35, 75, 84, 203/DIG. 3; 260/465.9

[56] References Cited
UNITED STATES PATENTS

| 3,201,918 | 8/1965 | Sennewald et al. ............... 260/465.9 |
|---|---|---|
| 3,247,237 | 4/1966 | Hagemeyer et al. ............... 260/465.9 |
| 3,328,266 | 6/1967 | Modiano et al. ................... 260/465.9 |
| 3,328,268 | 6/1967 | Barrel .............................. 260/465.9 |
| 3,329,582 | 4/1967 | Sennewald et al. ............... 260/465.9 |
| 3,352,764 | 11/1967 | Tyler................................. 260/465.9 |
| 3,462,477 | 12/1970 | Caporali et al. .................. 260/465.9 |
| 3,535,849 | 10/1970 | Hausweiller et al ............. 260/465.9 |
| 3,636,067 | 1/1972 | Lovett et al. ..................... 260/465.9 |
| 3,636,068 | 1/1972 | Lovett et al. ..................... 260/465.9 |

Primary Examiner—Norman Yudkoff
Assistant Examiner—Frank Sever
Attorney, Agent, or Firm—Herbert D. Knudsen

[57] ABSTRACT

Substantial capital and operating cost savings and improved recovery of acrylonitrile and methacrylonitrile are realized by the recycle of the product column bottoms to the quench liquid of the reactor effluent quench system.

9 Claims, 1 Drawing Figure

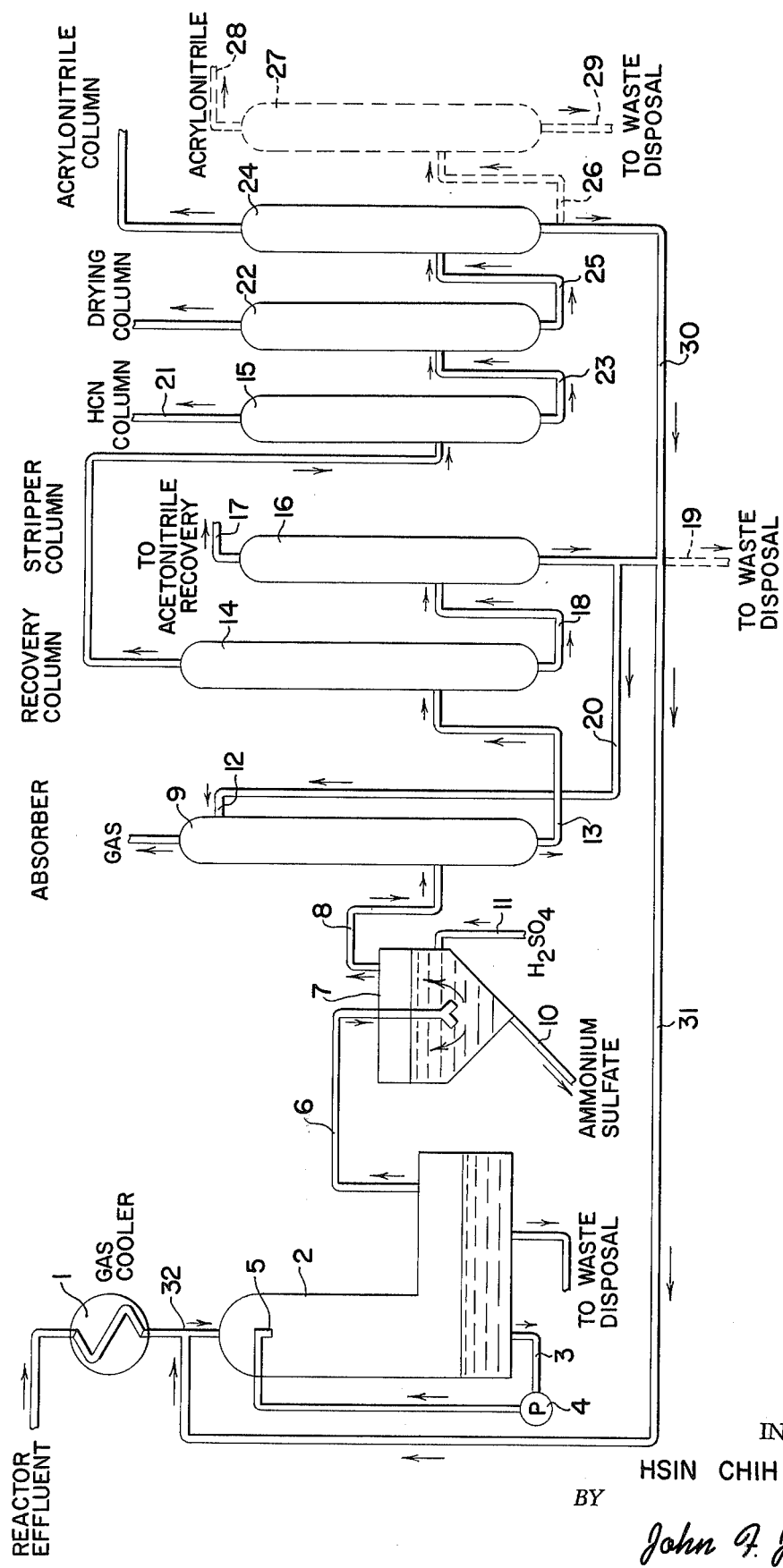

PROCESS FOR DISTILLATION AND RECOVERY OF OLEFINIC NITRILES

CROSS-REFERENCE TO RELATED APPLICATIONS

This application is a continuation-in-part of my prior application Ser. No. 132,008 filed Apr. 7, 1971, now abandoned.

BACKGROUND OF THE INVENTION

Recovery and purification systems for acrylonitrile and methacrylonitrile obtained by the ammoxidation of propylene or isobutylene are known, see for example U.S. Pat. Nos. 3,433,822; 3,399,120; and 3,535,849. The systems used involve the direct contact of the reactor effluent with an aqueous quenching liquid in a quenching system. In the quenching system, the reactor effluent is usually cooled to a temperature between about 90° to about 230°F.

The gases from the quenching system are then normally conducted to an absorber where the acrylonitrile or methacrylonitrile and water-soluble by-products are absorbed in water. The aqueous solution formed in the absorber is then treated in various distillation columns to obtain the desired product. The total system for recovery and purification may vary widely in the make-up of the individual components. Usually, however, they involve at least four components: one that removes acetonitrile; one that removes hydrogen cyanide; one that dries the acrylonitrile or methacrylonitrile product; and one that recovers the product. Many systems also use an ammonium sulfate recovery component. The particular components in the total recovery and purification system are not critical in the present invention.

SUMMARY OF THE INVENTION

It has now been discovered according to the present invention that substantial capital and operating cost savings can be realized along with improved recovery of acrylonitrile or methacrylonitrile by the recycle of the product column bottoms to form at least part of the quench liquid in the quench system. More specifically, this improvement in the recovery and purification of acrylonitrile or methacrylonitrile produced by the ammoxidation reaction of propylene or isobutylene, molecular oxygen and ammonia in the presence of an ammoxidation catalyst applies to the known system which consists of the steps of (a) contacting the ammoxidation reactor effluent with a quench liquid in a quench system to produce a gaseous quench effluent from said quench system having a temperature from about 90°F. to about 230°F.; (b) absorbing the gaseous quench effluent in water to form a solution and removing most of the by-products produced in the ammoxidation reaction and most of the water from the solution to obtain a crude acrylonitrile or crude methacrylonitrile product; and (c) distilling the crude acrylonitrile or crude methacrylonitrile to obtain an overhead stream of product-quality acrylonitrile or methacrylonitrile and a bottoms stream containing acrylonitrile or methacrylonitrile and impurities. The invention as applied to this known recovery and purification comprises recycling at least part of the bottoms stream obtained in step (c) and using this bottoms stream as at least part of the quench liquid in step (a). This improvement of the present invention saves the capital cost of a fractional distillation column that has been employed in the art and saves the operating expense of this eliminated column. Moreover, the efficiency of the recovery and purification system is improved.

The central aspect of the present invention is the recycle of the product column bottoms to form at least part of the quench liquid in the quenching step of the recovery and purification of acrylonitrile or methacrylonitrile.

The process of the present invention is applicable to any system that has two components: the first of which is a quench system and the second of which is a final product distillation column. Of course, all recovery and purification systems contain a number of intermediate separation and purification steps, but the exact nature of these steps is not critical in the present invention.

The first critical point of the recovery and purification is the quench system. The quench system in the recovery and purification scheme directly contacts a quench liquid with the effluent from the ammoxidation reactor. The reactor effluent gas usually has a temperature between about 700° and 900°F. Normally, this reactor effluent gas is cooled to a temperature of about 450°F. in a gas cooler. Cooling to gas temperatures below 450°F., in indirect contact coolers however, is undesirable because of deposits that form on the cooler surfaces.

In the quench system, the effluent from the ammoxidation reactor is cooled to a temperature of about 90° to about 230°F. In the preferred practice of the invention, the reactor effluent is cooled to a temperature of about 100° to about 210°F. and in the most preferred practice of the invention, the reactor effluent is cooled to about 200°F. These temperatures are attained by controlling the flow rate and temperature of the quench liquid in relation to the flow rate and temperature of the gas quenched.

The quench system effluent goes to an intermediate system that is not critical in the present invention. The intermediate system normally consists of an absorber where the water-soluble products are dissolved to form a solution, and a number of distillation columns where the components of the solution are separated and purified. This intermediate system is not critical to the present invention because this recovery, separation and purification can be conducted by a number of known techniques.

In the present invention, however, the most preferred separation and purification of the solution formed in the absorber consists of the steps of (i) passing the solution into a distillation column where distillation is conducted to produce a gaseous overhead stream containing acrylonitrile or methacrylonitrile, HCN and water and a liquid bottoms stream containing acetonitrile and water; (ii) condensing said gaseous stream and allowing an aqueous layer and an organic layer to form; (iii) transferring the organic layer to a distillation column and distilling the organic layer to produce a gaseous overhead product that contains substantially all of the HCN, and a liquid bottoms stream that contains acrylonitrile or methacrylonitrile and water; and (iv) transferring the bottoms stream from (iii) to a distillation column wherein the water is removed as overhead and crude acrylonitrile or crude methacrylonitrile is produced in a bottoms stream. This preferred intermediate treatment could be replaced by any one of a number of known systems for producing a crude nitrile product from the absorber solution.

The second critical step in the recovery and purification is the step where the crude acrylonitrile or crude methacrylonitrile is distilled in a distillation column, also called a product column, to produce product-quality acrylonitrile or methacrylonitrile. In this distillation column, distillation is conducted to obtain a gaseous overhead stream of product-quality acrylonitrile or methacrylonitrile and a liquid bottoms stream containing acrylonitrile or methacrylonitrile and impurities.

The exact nature of the impurities varies widely depending upon the nature of the processing that has preceded the last distillation. In the present invention, the exact composition of these impurities is not critical because they have been found to have a beneficial rather than deleterious effect on the quench system.

The invention involves the critical quench system and critical product distillation column. In the invention, at least part of the product distillation column bottoms are recycled and used as at least part of the quench liquid in the quench system.

This invention results in significant capital and operating savings. Normally, the product distillation column bottoms are fed to another distillation column where further product is recovered as overhead, and the liquid bottom stream is discarded. Use of the present invention saves the capital and operating expense of this column. Moreover, the waste stream from this extra distillation contains valuable chemicals that are desirable additions to the quench column. Further, the elimination of the waste stream from this second column concentrates waste effluent so that treatment to remove polluting contaminants may be more easily effected.

In the most preferred practice of the present invention, a bottoms stream from the first distillation column after the absorber is purified further. This bottoms stream contains acetonitrile and water. This bottoms stream in this most preferred practice of the invention is fed to a distillation column wherein distillation is conducted to produce acetonitrile as a gaseous overhead stream, and a liquid bottoms stream containing water and impurities. At least part of this stream is also recycled to the quench system to form at least part of the quench liquid. Again, the exact nature of these impurities is not critical because they have been found to be acceptable in the quench system. In the past, the bottoms from this acetonitrile column have been discharged as waste in a separate stream. Now, however, according to this most preferred aspect of the present invention, this separate waste stream is eliminated. The waste streams are concentrated in one area, and that is the quench liquid bottoms. The concentration of these waste streams at one source provides a stream that has a relatively constant composition, thus simplifying waste treatment to remove organic pollutants, and it also provides one stream rather than a number of streams that must be collected.

In the practice of the invention, all of the product column bottoms and all of the acetonitrile column bottoms that would normally be sent to waste treatment are recycled to become a part of the quench liquid in the quench system. The pH of these recycle streams is normally between 3 and less than 7 as a result of the recovery and purification process. If necessary, an organic acid, such as acetic acid or oxalic acid could be used to maintain an acidic pH.

DESCRIPTION OF THE DRAWING

Referring to the drawing, which is a flow sheet, one embodiment of my improved recovery and purification process is shown in the solid lines and prior art processes are indicated in the dotted lines. According to my invention, the effluent from the ammoxidation reactor (not shown) wherein propylene is treated with ammonia and molecular oxygen in the vapor phase over an ammoxidation catalyst enters a gas cooler 1 in which it is cooled from a temperature of about 800°F. to about 450°F. The effluent from the gas cooler, 1, enters a quench system which consists of a recycle stream (to be described later) sprayed into the gas at point 32 and a gas washer 2. The gas washer 2 contains an aqueous liquid in the bottom thereof which is held at a temperature of about 180°F. Said aqueous liquid is continuously cycled through passage, 3, by means of pump, 4, to a spray nozzle, 5, near the top of the washer, 2, where the aqueous liquid spray contacts the incoming reactor effluent. The recycle stream could be added to this aqueous liquid between pump, 4, and spray nozzle, 5, by a line not shown. The high-boiling material from the reactor effluent is deposited in the aqueous liquid in the bottom of the gas washer, 2, and the volatile materials in the effluent are passed as vapor through a line, 6, into a bubble chamber, 7, containing aqueous sulfuric acid wherein most of the ammonia in the effluent is converted to ammonium sulfate.

The aqueous sulfuric acid in the chamber, 7, is maintained at a temperature of about 180°F., and the volatile products other than ammonia continue through line, 8, into an absorber, 9. The level of aqueous sulfuric acid in the bubble chamber, 7, is maintained substantially constant by the continuous withdrawal of ammonium sulfate solution at the bottom, 10, and addition of fresh sulfuric acid through line, 11. In the absorber, 9, a stream of water at, 12, contacts the gaseous stream from, 8, and the water-soluble material is taken off at the bottom of the absorber column, 9, through line, 13, and is conducted to the recovery column, 14, wherein a light overhead is collected and transferred to the HCN column, 15, and the bottoms from the recovery column, 14, go to the stripper column, 16, through line, 18.

From the stripper column, 16, there is withdrawn an overhead, 17, to by-product acetonitrile recovery. The major portion of the bottoms from the stripper column is transmitted by line, 20, back to the absorber column, 9, at point, 12, previously described. The remaining portion, which was formerly taken to waste disposal, 19, is now taken to point, 32, through line, 31, and sprayed into the reactor effluent.

In the further processing of the acrylonitrile, the HCN is removed as overhead, 21, in the HCN column, 15, and the bottoms from this column are transmitted to a drying column, 22, through line, 23. In the drying column, 22, water is removed as the overhead and the bottoms go to the acrylonitrile column, 24, through line, 25. Acrylonitrile is recovered as the overhead from the acrylonitrile column, 24.

According to the prior art procedure, the bottoms from the acrylonitrile column were transferred by line, 26, to a second distillation column, 27, wherein acrylonitrile was taken as overhead, 28, and the bottoms went to waste disposal through line 29. In my process, however, the bottoms from column, 24, which are normally slightly acidic (pH about 3–5) are conducted through line, 30, into the line, 31, and back to point, 32, where they are mixed with the reactor effluent which has just been cooled in the gas cooler, 1, which then enters the gas washer, 2, and completes the recovery cycle. Alternatively, this recycle stream could be sprayed through nozzle, 5, rather than at point, 32.

As described in U.S. Pat. No. 3,433,822, the reactor effluent was previously cooled to as low as 340°F. in a tube cooler before it enters the gas washer. However, at this low temperature, significant fouling of the tube cooler occurs because some of the high-boiling compounds in the effluent condense on the cooler tube walls and cause fouling of the tubes. In spite of the fact that liquid from the bottom of the gas washer was frequently sprayed into the cooler tubes to flush the greasy materials out during the operation, the operation of the reactor has had to be stopped from time to time in order to clean the cooler tubes properly.

It has been found in the invention that the condensation of high-boiling materials from the reactor effluent is significantly less when the gases from the cooler are maintained at a temperature of about 450°F. or higher. It is thus advantageous not to cool the reactor effluent below a temperature of about 450°F. in the gas cooler unit. This 450°F. or higher gas coming from the gas cooler is introduced into the section of a jet washing device through which a large amount of water from the sump of the gas washer is circulated and sprayed into the reactor effluent to abosorb and condense the high-boiling compounds present therein. Most of the other products in the reactor effluent such as acrylonitrile, acetonitrile, hydrogen cyanide, propionitrile and unreacted ammonia remain in the gas phase of the reactor effluent in the gas washer.

The washing water from the bottom of the gas washer can be cooled externally before it enters the spray nozzle so that the temperature of the reactor effluent in the gas washer can be controlled to cause a partial condensation of the water vapor reactor product present in the reactor effluent. In other words, the temperature of the washing water in the gas washer is maintained somewhat lower than the dew point temperature of the reactor effluent.

A flow of water equivalent to the amount condensed out from the reactor effluent is continuously withdrawn as waste from the bottom of the gas washer in order to maintain a proper liquid level in the sump of the gas washer. There is usually about 20% by weight of greasy high-boiling materials in the waste water drawn off from the bottom of the gas washer, and this material is disposed of usually by incineration.

In another case, the washing water from the bottom of the gas washer is not externally cooled. It is partially flashed in the gas washer. This quenches the reactor effluent from 450°F. down to about 180°F. After the high-boiling compounds are removed, the reactor effluent is sent to the next processing equipment with a higher content of water vapor. The addition of water into the sump of the gas washer, therefore, is required in order to maintain a proper liquid level in the sump of the gas washer. The flow of this water addition is maintained large enough to also compensate for the draw-off of a water stream from the sump. The draw-off water stream which contains about 20% of greasy materials is normally burned and disposed of in an incinerator.

In any case, the loss of acrylonitrile in the recovery and purification of acrylonitrile prepared by the ammoxidation of propylene in prior art processes is usually in the order of 2.5% or even higher.

I have discovered that the recycle streams of the present invention substantially reduce this acrylonitrile loss. In the art processes, the significant amount of ammonia dissolved in the washing water causes an alkaline pH, usually around 8.5. This alkaline condition of the water leads to polymerization and condensation reactions between ammonia, acrylonitrile, hydrogen cyanide and carbonyl compounds and other compounds present in the reactor effluent when the reactor effluent is contacted with the washing water. Higher effluent temperatures in the gas washer also lead to more polymerization and condensation of materials in the effluent. These forces are counterbalanced by the present invention.

By the use of the present invention, the loss of acrylonitrile has been reduced from about 2.5% of the acrylonitrile present in the reactor effluent to an amount of only about 1.1%. Although this is a relatively minor difference in percentage, i.e. 1.4%, the percentage reduction is well over 50%, and the commercial ramifications of this improvement result in the savings of literally millions of pounds of useful acrylonitrile product per year.

I claim:
1. In the process for the recovery and purification of acrylonitrile produced by the ammoxidation reaction of propylene, molecular oxygen and ammonia in the presence of ammoxidation catalyst which consists of the steps of;
   a. contacting the ammoxidation reactor effluent with an aqueous quench liquid in a quench system to produce a gaseous quench effluent from said quench system having a temperature of about 90° to about 230°F.;
   b. removing the gaseious quench effluent from said quench system and absorbing said removed gaseous quench efflluent in water to form a solutionn and distilling most of the by-products produced in the ammoxidation reaction and most of the water from said solution to obtain a liquid stream containing crude acrylonitrile; and
   c. distilling the crude acrylonitrile to obtain a gaseous overhead stream of product-quality acrylonitrile and a bottoms stream containing acrylonitrile and impurities and having a pH of about 3–5, the improvement comprising:
   recycling part of said liquid bottoms stream obtained in step (c) and using said liquid bottoms stream as at least part of said quench liquid in step (a).
2. The process of claim 1 wherein the temperature of the effluent from the quench system is about 100° to about 210°F.
3. The process of claim 1 wherein the temperature of the gaseous effluent from the quench system is about 200°F.
4. The process of claim 1 wherein the removal of by-products and water from the solution of step (b) consists of the steps of (i) passing said solution into a distillation column where distillation is conducted to produce a gaseous overhead stream containing acrylonitrile, HCN and water and a liquid bottoms stream containing acetonitrile; (ii) condensing said gaseous stream and allowing an aqueous layer and an organic layer to form; (iii) transferring said organic layer to a distillation column and distilling the organic layer to produce a gaseous overhead product that contains substantially all of the HCN and a liquid bottoms stream that contains acrylonitrile and water; and (iv) transferring said bottoms stream from (iii) to a distillation column wherein the water is removed as overhead and crude acrylonitrile or crude methacrylonitrile is produced in a bottoms stream.

5. The process of claim 4 wherein said liquid stream containing acetonitrile from step (i) is transferred to an acetonitrile distillation column and distillation is conducted to remove an overhead stream containing acetonitrile and wherein at least part of the bottoms from said acetonitrile distillation column are used as part of said quench liquid in step (a).

6. The process of claim 1 wherein all of said liquid bottoms stream obtained in step (c) are recycled to step (a) and used as at least part of the quench liquid.

7. The process of claim 6 wherein the pH of all liquid bottoms streams recycled to the quench system as part of the quench liquid is maintained between 3 and less than 7.

8. The process of claim 1 wherein said ammoxidation reactor effluent has a temperature of at least 450°F. prior to contact with the quench liquid.

9. In the process for the recovery and purification of methacrylonitrile produced by the ammoxidation reaction of isobutylene, molecular oxygen and ammonia in the presence of ammoxidation catalyst which consists of the steps of:

a. contacting the ammoxidation reactor effluent with an aqueous quench liquid in a quench system to produce a gaseous quench effluent from said quench system having a temperature of about 90° to about 230°F.;

b. removing the gaseous quench effluent from said quench system and absorbing said removed gaseous quench effluent in water to form a solution and distilling most of the by-products produced in the ammoxidation reaction and most of the water from said solution to obtain a liquid stream containing crude methacrylonitrile; and c. distilling the crude methacrylonitrile to obtain a gaseous overhead stream of product-quality methacrylonitrile and a bottoms stream containing methacrylonitrile and impurities and having a pH of about 3–5, the improvement comprising:

recycling part of said liquid bottoms stream obtained in step (c) and using said liquid bottoms stream as at least part of said quench liquid in step (a).

* * * * *